(12) United States Patent
Schumacher et al.

(10) Patent No.: US 10,251,682 B2
(45) Date of Patent: Apr. 9, 2019

(54) DISTAL RADIUS NAIL

(71) Applicant: DEPUY SYNTHES PRODUCTS, INC., Raynham, MA (US)

(72) Inventors: Yvonne Schumacher, Solothurn (CH); Robert Frigg, Bettlach (CH); Alfred Niederberger, Bettlach (CH); Daniel Fluri, Bettlach (CH); Andreas Appenzeller, Bettlach (CH); Beat Spörri, Zofingen (CH)

(73) Assignee: Depuy Synthes Products, Inc., Raynham, MA (US)

( * ) Notice: Subject to any disclaimer, the term of this patent is extended or adjusted under 35 U.S.C. 154(b) by 15 days.

(21) Appl. No.: 15/466,105

(22) Filed: Mar. 22, 2017

(65) Prior Publication Data

US 2018/0271567 A1 Sep. 27, 2018

(51) Int. Cl.
*A61B 17/72* (2006.01)
*A61B 17/17* (2006.01)
*A61B 17/16* (2006.01)
*A61B 17/88* (2006.01)

(52) U.S. Cl.
CPC .......... *A61B 17/72* (2013.01); *A61B 17/1725* (2013.01); *A61B 17/725* (2013.01); *A61B 17/16* (2013.01); *A61B 17/1782* (2016.11); *A61B 17/88* (2013.01)

(58) Field of Classification Search
CPC ....................................... A61B 17/72–17/7291
See application file for complete search history.

(56) References Cited

U.S. PATENT DOCUMENTS

| | | |
|---|---|---|
| 6,210,414 B1 | 4/2001 | Lin |
| 6,527,775 B1 | 3/2003 | Warburton |
| 6,629,976 B1 | 10/2003 | Gnos et al. |
| 6,702,823 B2 | 3/2004 | Iaia |
| 6,706,046 B2 | 3/2004 | Orbay et al. |

(Continued)

FOREIGN PATENT DOCUMENTS

| | | |
|---|---|---|
| DE | 4318150 | 12/1994 |
| EP | 0086552 B1 | 7/1986 |

(Continued)

*Primary Examiner* — Nicholas J Plionis
*Assistant Examiner* — Steven J Cotroneo
(74) *Attorney, Agent, or Firm* — Fay Kaplum & Marcin, LLP

(57) ABSTRACT

A system for treating a bone fracture includes an intramedullary nail sized and shaped to be inserted through a medullary canal of a bone to extend across a fracture site of the bone, the intramedullary device extending from a first end to a second end and including a plurality of openings extending laterally therethrough, the openings sized and shaped to receive bone fixation elements therethrough, and an insertion device including a base portion and a handle portion extending therefrom, the base portion integrally formed with the intramedullary nail and connected thereto via a plurality of connection points which, when a force is exerted thereon, break to disconnect the insertion device from the intramedullary nail, the base portion including a plurality of guide channels extending therethrough, each of the guide channels being aligned with a corresponding one of the openings of the intramedullary nail.

14 Claims, 3 Drawing Sheets

(56) References Cited

U.S. PATENT DOCUMENTS

Figure 1:
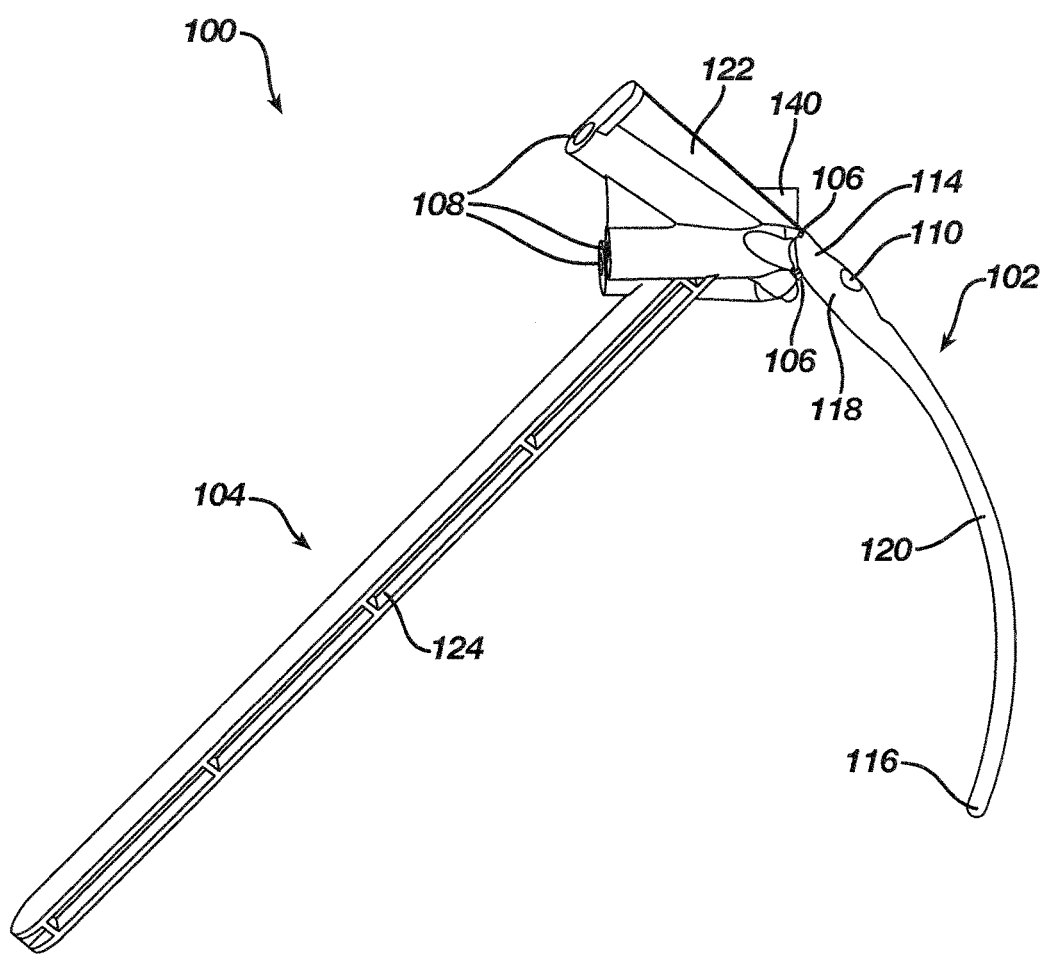

| | | |
|---|---|---|
| 6,793,659 B2 | 9/2004 | Putnam |
| 7,160,302 B2 | 1/2007 | Warburton |
| 7,588,577 B2 * | 9/2009 | Fencl .................. A61B 17/1659 606/104 |
| 7,713,271 B2 | 5/2010 | Warburton |
| 7,727,264 B2 | 6/2010 | Orbay et al. |
| 8,092,453 B2 | 1/2012 | Warburton |
| 8,100,910 B2 | 1/2012 | Warburton |
| 8,216,238 B2 | 7/2012 | Tellman |
| 8,419,735 B2 | 4/2013 | Appenzeller et al. |
| 9,050,114 B2 | 6/2015 | Giannoudis |
| 2003/0073999 A1 | 4/2003 | Putnam |
| 2004/0049192 A1 | 3/2004 | Shimizu |
| 2008/0119849 A1 * | 5/2008 | Beardsley .......... A61B 17/7032 606/306 |
| 2008/0183171 A1 | 7/2008 | Elghazaly et al. |
| 2009/0248024 A1 * | 10/2009 | Edwards ............ A61B 17/1725 606/62 |
| 2009/0292292 A1 | 11/2009 | Fencl et al. |
| 2010/0234846 A1 | 9/2010 | Eglseder |
| 2011/0112534 A1 * | 5/2011 | Appenzeller ...... A61B 17/7233 606/62 |
| 2012/0059376 A1 * | 3/2012 | Rains .................... A61B 17/72 606/62 |
| 2012/0253410 A1 | 10/2012 | Taylor et al. |
| 2014/0066932 A1 * | 3/2014 | Appenzeller ...... A61B 17/1725 606/64 |

FOREIGN PATENT DOCUMENTS

| | | |
|---|---|---|
| EP | 0772420 B1 | 10/2000 |
| EP | 1329197 B1 | 9/2004 |
| EP | 1808143 A1 | 7/2007 |
| EP | 1656899 B1 | 9/2008 |
| EP | 1937171 B1 | 3/2010 |
| EP | 2174611 B1 | 12/2010 |
| EP | 1765207 B1 | 7/2011 |
| EP | 2427131 B1 | 6/2013 |
| EP | 1507486 B1 | 11/2013 |
| EP | 1855605 B1 | 1/2014 |
| EP | 1095626 B1 | 2/2016 |
| EP | 2482739 B1 | 7/2016 |
| GB | 2473960 B | 7/2013 |

* cited by examiner

DISTAL RADIUS NAIL

BACKGROUND

A distal radius fracture may be treated using an intramedullary nail inserted into a medullary canal of the radius. Screws may be inserted through laterally extending openings in the intramedullary nail to fix the nail relative to the bone and stabilize the fracture. An insertion instrument is generally used for the insertion of an intramedullary nail to bring the intramedullary nail to an entry point of the bone. Insertion instruments may also be used for guiding screws or other fixation elements into laterally extending openings of the nail. Thus, solutions for the treatment of distal radius fractures are often judged based on how well the insertion device works with the intramedullary nail.

SUMMARY

The present embodiments are directed to a system for treating a bone fracture comprising an intramedullary nail sized and shaped to be inserted through a medullary canal of a bone to extend across a fracture site of the bone, the intramedullary device extending from a first end including a head portion to a second end, a shaft of the intramedullary device extending from the head portion to the second end, the intramedullary device including a plurality of openings extending laterally therethrough, the openings sized and shaped to receive bone fixation elements therethrough and an insertion device including a base portion and a handle portion extending therefrom, the base portion integrally formed with the intramedullary nail and connected thereto via a plurality of connection points which, when a force is exerted thereon, break to disconnect the insertion device from the intramedullary nail, the base portion including a plurality of guide channels extending therethrough, each of the guide channels being aligned with a corresponding one of the openings of the intramedullary nail.

The present embodiments are also directed to a method for treating a distal radius bone, the method comprising drilling an entry hole through a styloid process of a distal radius bone, inserting an intramedullary nail through the entry hole using an insertion device integrally formed with the intramedullary nail until a shaft portion of the intramedullary nail is passed into a medullary canal of the bone and a head portion of the intramedullary nail resides within an end of the bone, the intramedullary nail connected to the insertion device via a plurality of connection points, drilling holes into the bone via guide channels of the insertion device which are in alignment with openings of the intramedullary nail, inserting bone fixation elements through drilled holes of the bone and into a corresponding one of the openings, and snapping off the insertion device to disconnect the insertion device from the intramedullary nail by breaking the connection points connecting the insertion device and the intramedullary nail.

BRIEF DESCRIPTION

Figure 2:
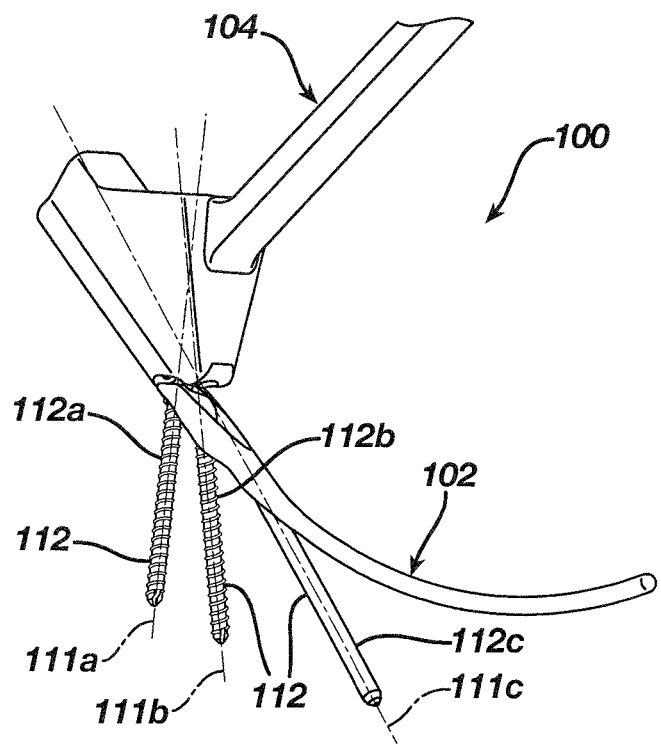
Figure 3:
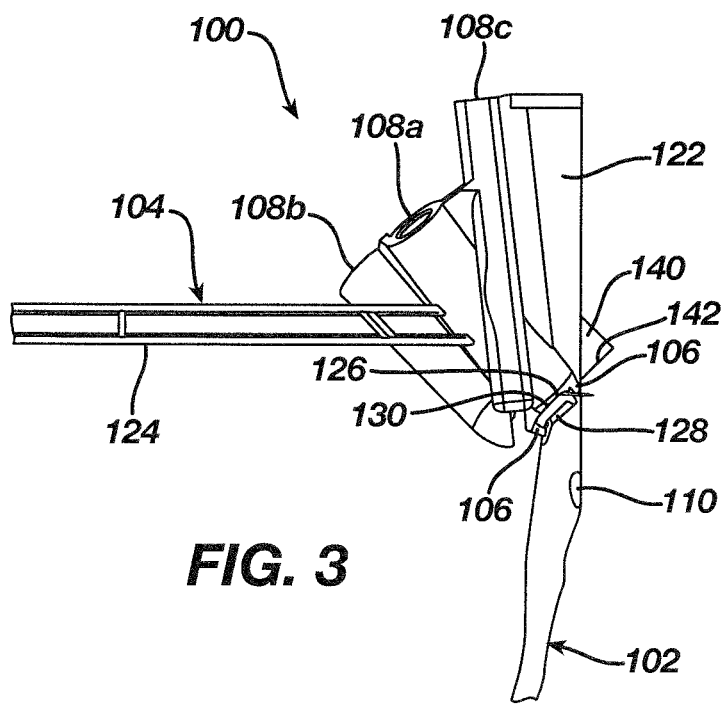
Figure 4:
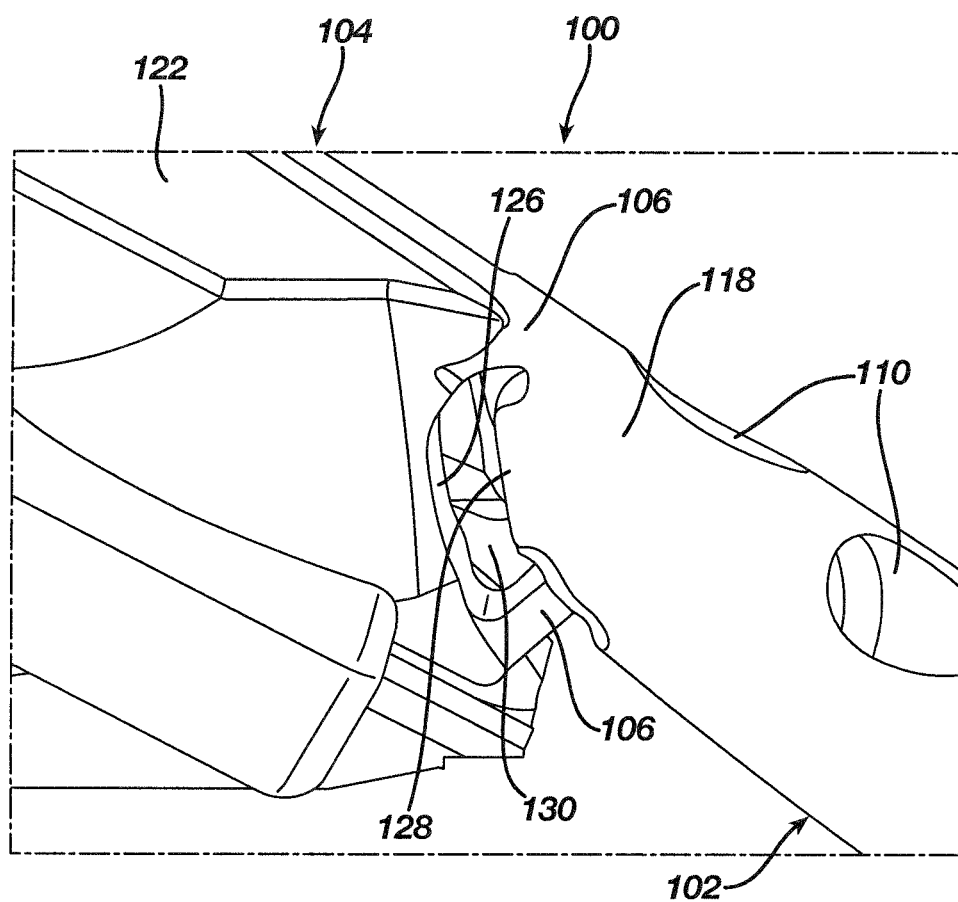
Figure 5:
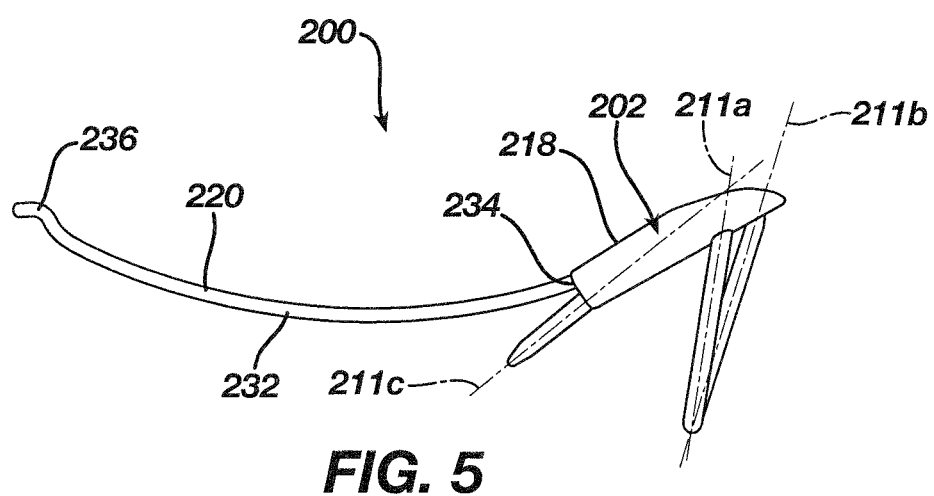

FIG. 1 shows a side view of a system according to an exemplary embodiment;
FIG. 2 shows a perspective view of the system of FIG. 1;
FIG. 3 shows another side view of the system of FIG. 1;
FIG. 4 shows an enlarged perspective view of the system of FIG. 1; and FIG. 5 shows a perspective view of an intramedullary nail of a system according to another exemplary embodiment.

DETAILED DESCRIPTION

The present embodiments may be understood with reference to the following description and the appended drawings, wherein like elements are referred to with the same reference numerals. The present embodiment relates to the treatment of bone and, in particular, relates to treatments using an intramedullary nail. Exemplary embodiments describe a system comprising an intramedullary nail and insertion device that are integrally formed with one another so that, upon insertion of the intramedullary nail into, for example, a distal radius, the insertion device may be Asnapped@ off, leaving the intramedullary nail within the bone. Although the exemplary embodiments describe the system as being used to treat the distal radius, it will be understood by those of skill in the art that the system of the embodiments may also be used to treat other bones such as, for example, the fibula.

As shown in FIGS. 1-4, a bone fixation system 100 according to an exemplary embodiment comprises an intramedullary nail 102 and an insertion device 104 integrally formed and connected to one another via a plurality of connection points 106 for the treatment of a fractured bone such as, for example, a fracture of the distal radius. The insertion device 104 includes a plurality of guide channels 108 extending therethrough, each of the guide channels 108 being aligned with a corresponding opening 110 extending laterally through the intramedullary nail 102, so that drill guides (not shown) may be received within the guide channels 108 and the openings 110. Upon insertion of the intramedullary nail 102 into the bone, a drilling device may be inserted through the drill guides to drill holes into the bone, so that bone fixation elements 112 may be inserted through the holes and into the openings 110 of the intramedullary nail 102 to fix the intramedullary nail 102 relative to the bone and to stabilize a fracture of the bone. In particular, a fixation element 112 is inserted through one of the openings 110 so that a shaft thereof locks into the bone. The fixation elements 112 are capable of angular stability relative to the intramedullary nail 102 by deforming a material of the intramedullary nail 102. Once the intramedullary nail 102 has been fixed in the bone, the insertion device 104 may be Asnapped@ off without the use of tools, breaking the connection points 106 and leaving the intramedullary nail 102 implanted in the bone, as will be described in further detail below.

The intramedullary nail 102 is sized and shaped to be inserted into a medullary canal of, for example, the distal radius. The intramedullary nail 102 may, for example, be particularly suited for treating extra-articular fractures of the distal radius so that, when inserted into the medullary canal of the bone, the intramedullary nail 102 extends across the fracture to fix the separated or fractured portions of bone relative to one another. The intramedullary nail 102 extends longitudinally from a first end 114 to a second end 116 and includes a head portion 118 at the first end 114 and a shaft portion 120 extending longitudinally therefrom toward the second end 116. The shaft portion 120 may extend along a curve to facilitate insertion of the intramedullary nail 102 into the medullary canal of the bone via a hole drilled through, for example, a styloid process of the bone.

The intramedullary nail 102 includes a plurality of openings 110 extending laterally therethrough, the openings 110 configured to receive bone fixation elements 112 therein for fixing the intramedullary nail 102 relative to the bone. In one exemplary embodiment, the intramedullary nail 102 may have three openings 110 extending laterally through the head portion 118 of the intramedullary nail 102. A first and second one of the openings 110 may extend along first and second axes 111a, 111b, respectively, that are angled and distanced from one another about and along a longitudinal axis of the intramedullary nail 102 to fix the intramedullary nail 102 relative to the bone. Thus, when the intramedullary nail 102 is used to fix a distal radius, first and second bone fixation elements 112a, 112b inserted along the first and second axes 111a, 111b through the first and second openings 110 extend through a distal end of the bone. A third one of the openings 110 is distanced from the first and second openings along the longitudinal axis of the intramedullary nail 102 and extends along a third axis 111c which extends across a fracture of the bone. Thus, when a third bone fixation element 112c is inserted along the third axis 111c through the third opening 110, the third bone fixation element 112c extends across the fracture to provide further stabilization of the fracture. Although the exemplary embodiment shows and describes a specific configuration of openings 110, it will be understood by those of skill in the art that the intramedullary nail 102 may have any number of openings 110 extending therethrough in any of a variety of configurations.

Current bone fixation systems include an intramedullary nail that is attached, for insertion, to a separate insertion device via screws which are removed upon insertion of the intramedullary nail into the bone so that the insertion device may be separated from the nail and removed from the body. The intramedullary nail 102 of the system 100 of the present embodiment, however, includes an insertion device 104 integrally formed with the nail 102 to simplify the insertion of the nail 102 and the removal of the insertion device 104 from the nail 102. The fixation system 100 may be formed of a material such as, for example, PEEK, and may be injection molded together so that the connection points 106 are formed by a flow of material between the intramedullary nail 102 and the insertion device 104 during the molding process.

The insertion device 104 includes a base portion 122 and a handle member 124 extending therefrom. The guide channels 108 extend through the base portion 122 in alignment with the openings 110 of the intramedullary nail 102. In other words, each of the guide channels 108 extends along an axis which is coaxial with the axis of a corresponding one of the openings 110 of the intramedullary nail 102. In the embodiment shown, the insertion device 104 includes three guide channels 108—an axis of a first channel 108a is aligned with the first axis 111a of the first opening 110a, an axis of a second channel 108b is aligned with the second axis 111b of the second opening 110b and an axis of a third channel 108c is aligned with the third axis 111c of the third opening 110c. It will be understood by those of skill in the art, however, that the insertion device 104 may have any number of guide channels 108 so long as the number of guide channels 108 corresponds to the number of openings 110 of the intramedullary nail 102.

In a further embodiment, the insertion device 104 includes a stop element 140 extending from a portion thereof. In one exemplary embodiment, as shown in FIGS. 1 and 3, the stop element 140 is configured as a fin-shaped protrusion extending from a portion of the insertion device 104 substantially opposing the handle member 124. The stop element 140 may be shaped such that a bone-facing surface 142 thereof extends substantially parallel to the insertion device facing surface 128 of the intramedullary nail 102.

The base portion 122 of the insertion device 104 is connected to the head portion 120 of the intramedullary nail 102 at a plurality of connection points 106. The base portion 122 is connected to the head portion 120 of the intramedullary nail 102 such that an intramedullary nail facing surface 126 of the base portion 122 is separated from an insertion device facing surface 128 of the head portion of the intramedullary nail 102 by a gap of a predetermined distance. In one exemplary embodiment, the nail facing surface 126 may be separated from the insertion device facing surface 128 by a distance of between approximately 0.8 mm and 1.0 mm. It will be understood by those of skill in the art, however, that this distance is exemplary only, and that the distance between the nail facing surface 126 and the insertion device facing surface 128 may vary depending on a desired length of the connection points 106. A size of the gap may, for example, be determined by a desired nail insertion depth. Additional factors for determining the size of the gap may include material properties and manufacturing techniques (e.g., mold design and capabilities).

The system 100 may include any number of connection points 106 connecting the insertion device 104 and the intramedullary nail 102. In a preferred embodiment, however, the system 100 includes two or three connection points 106 at which the base portion 122 is connected to the head portion 120 of the intramedullary nail 102. The connection points 106 in this embodiment extend from an outermost edge of the insertion device facing surface 128 to the nail facing surface 126 of the base portion 122 of the insertion device 104 so that the connection points 106 do not interfere with the guide channels 108 and the openings 110 of the insertion device 104 and the intramedullary nail 102, respectively. It will be understood by those of skill in the art, however, that the configuration of the connection points 106 described above is exemplary only may vary depending on the manufacturing process and material properties.

The connection points 106 are sized and shaped so that, upon implantation of the intramedullary nail 102 into the bone, the connection points 106 may be broken by pulling the insertion device 104 toward a user of the device while angling, rotating or otherwise moving the insertion device 104 relative to the intramedullary nail 102. In one exemplary embodiment, a cross-sectional thickness of a portion of the connection points 106 to be broken may range from between 0.4 mm to 1.2 mm. The connection points 106 may have any of a variety of sizes and dimensions, however, so long as the connection points 106 are configured to facilitate manual breakage thereof by a user once the insertion procedure has been completed. In one exemplary embodiment, a distance between the insertion device facing surface 128 and the nail facing surface 126 and the structure of the connection points 106 is defined via notches 130 formed between the base portion 122 of the insertion device 104 and the head portion 118 of the intramedullary nail 102. The notches 120 are sized and shaped to define the distance between the surfaces 128, 126 and to define the size and shape of the connection points 106 to facilitate breakage of the connection points 106 at a desired point therealong when subjected to a predetermined force. For example, as shown in FIG. 4, the notches 130 are formed so that the connection points 106 are more robust (thicker) on the side of the base portion 122 of the insertion device 104 than on the side of the intramedullary nail 102. Thus, the connection points are configured to break closer to the intramedullary nail 102 than to the insertion device 104. Thus, as will be understood by those of skill in the art, the size and shape of the notches 130 and/or the connection points 106 predetermines a breaking point of the connection points 106. In one exemplary embodiment, as described above, the notches 130 and the connection points 106 are sized and shaped to facilitate breakage of the connection points 106 so that, upon breakage, no portion of the intramedullary nail 102, and/or portions of the connection points 106 that remain connected thereto, protrudes beyond an exterior surface of the bone. Also, as would be understood by those skilled in the art, any small protrusion from the nail 102 remaining at a connection point 106 may be filed down or otherwise removed or smoothed as desired.

Due to the breakable (e.g., Afragile@) nature of the connection points 106, the intramedullary nail 102 may be inserted into the bone with drill guides inserted into the guide channels 108 and the openings 110 of the insertion device 104 and the intramedullary nail 102, respectively. In this exemplary embodiment, the fixation system 100 may be pre-assembled with the drill guides inserted through the first and second guide channels 108a, 108b and the openings 110. Insertion of the drill guides in these channels 108a, 108b and their corresponding openings 110 does not interfere with the implantation of the intramedullary nail 102. The guide channel 108c may be left open during the initial implantation of the intramedullary nail 102. When the drill guides are inserted into the guide channels 108a, 108b and the corresponding openings 110, the drill guides extend across the space between the insertion device facing surface 128 and the nail facing surface 126, restricting movement between the insertion device 104 and the nail 102 and preventing breakage of the connection points 106.

According to an exemplary surgical technique for fixing a fracture of a bone, such as the distal radius, using the system 100, an entry hole is drilled through the styloid process of the radius using known methods in the art. For example, a guide may be placed over the radial styloid and a guide wire may be inserted therethrough. A cannulated drill may be slid over the guide wire to drill the entry hole. Once the entry hole has been created, the shaft portion 120 of the intramedullary nail 102 is inserted through the entry hole and moved into the medullary canal of the bone by gripping the handle member 124 of the insertion device 104. As described above, to provide additional stability between the insertion device 104 and the intramedullary nail 102, the intramedullary nail 102 is inserted into the bone with the drill guides inserted into the guide channels 108 and the openings 110 of the insertion device 104 and the intramedullary nail 102, respectively. As would be understood by those skilled in the art, the curvature of the intramedullary nail 102 is selected to facilitate insertion of the intramedullary nail 102 into the medullary canal via the entry hole in the styloid process.

The intramedullary nail 102 is inserted into the bone until the base portion 122 of the insertion device contacts an exterior surface of the bone and/or the stop element 140 of the insertion device 104 contacts the exterior surface of the bone. A drill is then passed through the drill guides in the first and second drill channels 108a, 108b to drill holes in the bone, in alignment with the openings 110a, 110b. Once the holes have been drilled, the drill guides are removed and bone fixation elements (e.g., bone screws) are inserted through the guide channels 108a, 108b until head portions of the bone fixation elements engage the openings 110a, 110b and shaft portions of the bone fixation elements extend through the drilled holes into the bone. Upon fixing the intramedullary nail 102 relative to the bone via the bone fixation elements in the first and second openings 110a, 110b, a drill guide may be inserted through the third guide channel 108c and the third hole 110c in alignment with the axis of the third hole 110c. The drill guide may then be removed from the third guide channel 108c and a bone fixation element inserted through the third opening 110c so that the bone fixation element extends across the fracture site of the bone, providing further stability to the fracture fixation. In one exemplary embodiment, the bone fixation elements may be locking screws having threaded head portions that thread themselves into the material (e.g., PEEK) of the openings 110 to lock the screws relative thereto.

It will be understood by those of skill in the art that the above described steps regarding the drilling of holes in the bone and the insertion of bone fixation elements through the drilled holes is exemplary only and may differ according a number and position/orientation of openings 110 through the intramedullary nail 102. Once bone fixation elements have been inserted through a desired number of openings 110 in a desired configuration, the insertion device 104 is manually removed by breaking the connection points 106. In particular, the connection points 106 may be broken by angling, rotating or otherwise moving the insertion device 104 relative to the intramedullary nail 102. The insertion device 104 thus Asnaps off@ of the intramedullary nail 102 so that the insertion device 104 is decoupled from the intramedullary nail 102, leaving the intramedullary nail 102 implanted within the medullary canal of the bone. As described above, notches along a desired portion of the connection points 106 may facilitate breaking of the connection points 106 at a desired point therealong to prevent protrusion of any portion of the intramedullary nail 102 and/or connection point 106 beyond an exterior surface of the bone and damage to any surrounding tissue.

As shown in FIG. 5, a bone fixation system 200 according to another exemplary embodiment may be substantially similar to the system 100 described above, comprising an intramedullary nail 202 integrally formed with an insertion device (not shown) and connected to one another via connection points (not shown). The connection points may be formed substantially as described above with respect to the system 100. Similarly to the intramedullary nail 102, the intramedullary nail 202 may include a head portion 218 and a shaft portion 220. The shaft portion 220, however, is not formed of the same material as the remainder of the system (e.g., PEEK) but may be formed of a wire 232 extending therefrom. In one exemplary embodiment, the wire 232 may be formed of a stainless steel, the wire 232 extending from a first end 234 embedded within the head portion 218 toward a second end 236. In another embodiment, during manufacturing of the system 100, the wire 232 may be immersed in PEEK so that the wire is coated with the PEEK material.

The insertion device may be substantially similar to the insertion device 104 described above, comprising a base portion and handle extending therefrom. The base portion includes a plurality of guide channels extending therethrough to align with openings of the connected intramedullary nail 202. In one exemplary embodiment, axes of the guide channels are aligned with a corresponding one of a first axis 211a of a first opening 210, a second axis 211b of a second opening 210 and a third axis 211c of a third opening 210 so that holes corresponding to the openings 210 of the intramedullary nail 202 may be drilled via a drill inserted through the guide channels. The openings 210 may be configured in a manner substantially similar to the openings 110 of the system 100.

The system 200 may be used in a manner substantially similar to the system 100. Thus, when the system 200 is used to treat a fracture of the distal radius, the second end 236 of the wire 232 may be inserted through an entry hole drilled in the styloid process until the wire 232 is inserted into a medullary canal of the distal radius. As discussed above, in regard to the system 100, once implanted, the head portion 218 of the intramedullary nail 202 may extend through the distal end of the bone (e.g., distal radius) and the wire 232 may extend toward a proximal end of the bone. Holes may be drilled into the bone along axes 211*a*-211*c* so that bone fixation elements 212 may be inserted therealong into the bone, fixing the intramedullary nail 202 to the bone and/or providing further stabilization of the bone fracture. Upon implantation and fixation of the intramedullary nail 202, the insertion device is Asnapped off@ by breaking the connection points.

It will be understood by those of skill in the art that modifications and variations may be made in the structure and methodology of the present embodiment, without departing from the spirit or scope of the embodiments Thus, it is intended that the present embodiments cover the modifications and variations of these embodiments provided that they come within the cops of the appended claims and their equivalents.

What is claimed is:

1. A system for treating a bone fracture, comprising:
   an intramedullary nail sized and shaped to be inserted through a medullary canal of a bone to extend across a fracture site of the bone, the intramedullary device extending from a first end including a head portion to a second end, a shaft of the intramedullary device extending from the head portion to the second end, the intramedullary device including a plurality of openings extending laterally therethrough, the openings sized and shaped to receive bone fixation elements therethrough; and
   an insertion device including a base portion and a handle portion extending therefrom, the base portion formed as a single piece with the intramedullary nail and connected to the intramedullary nail via a plurality of connection points which, when a force is exerted thereon, break to disconnect the insertion device from the intramedullary nail, the base portion including a plurality of guide channels extending therethrough, each of the guide channels being aligned with a corresponding one of the openings of the intramedullary nail.

2. The system of claim 1, further comprising drill guides inserted through the guide channels of the insertion device and the corresponding openings of the intramedullary nail to provide further stability between the insertion device and the intramedullary nail.

3. The system of claim 1, wherein a nail facing surface of the base portion is separated from an insertion device facing surface at the first end of the intramedullary nail via a distance.

4. The system of claim 3, wherein the connection points extend from an outermost edge of the insertion device facing surface to the base portion.

5. The system of claim 3, wherein the connection points and the distance between the insertion device facing surface and the nail facing surface are defined via a notch extending between the base portion of the insertion device and the head portion of the intramedullary nail.

6. The system of claim 5, wherein the notch is sized and shaped to facilitate breakage of the connection points at a specific point therealong.

7. The system of claim 1, wherein the system includes two or three connection points.

8. The system of claim 1, wherein the system is molded via a PEEK material.

9. The system of claim 1, wherein the shaft is formed of a wire extending from the head portion toward the second end.

10. The system of claim 9, wherein the wire is formed of stainless steel.

11. The system of claim 9, wherein the wire is coated with a PEEK material.

12. The system of claim 1, wherein a first one of the openings and a second one of the openings extend through the head portion of the intramedullary nail along axes that are angled with respect to one another so that, when bone fixation elements are inserted through the first and second openings, the intramedullary nail is fixed relative to the bone.

13. The system of claim 1, wherein a third one of the openings extends through the intramedullary nail such that, when a bone fixation element is inserted along an axis thereof, the bone fixation element extends across a bone fracture to provide further stability to the fracture site.

14. The system of claim 1, wherein the shaft portion extends along a curve.

* * * * *